United States Patent [19]
Carroll et al.

[11] Patent Number: 5,296,192
[45] Date of Patent: Mar. 22, 1994

[54] DIAGNOSTIC TEST STRIP

[75] Inventors: Patrick J. Carroll, Ft. Lauderdale; Robin A. Wiscovitch, Coral Springs, both of Fla.

[73] Assignee: Home Diagnostics, Inc., Eatontown, N.J.

[21] Appl. No.: 862,733

[22] Filed: Apr. 3, 1992

[51] Int. Cl.$^5$ .............................................. G01N 21/00
[52] U.S. Cl. ...................................... 422/56; 422/58; 436/63; 436/164; 436/805
[58] Field of Search ................................... 422/56–58; 436/63, 164, 805, 14

[56] References Cited
U.S. PATENT DOCUMENTS
4,987,085 1/1991 Allen et al. .......................... 422/58

Primary Examiner—Lyle A. Alexander
Attorney, Agent, or Firm—Ralph T. Lilore

[57] ABSTRACT

Disclosed is a multi-layered test strip device for receiving whole blood on which a test for a suspected analyte is performed. The test confirms the presence, absence, or the amount of analyte, if present. The multi-layered device comprises two outside support layers between which are, in descending order relative to the horizontal plane, a) a spreading screen having defined characteristics, b) a separating layer which removes red blood cells at least partially via a red blood cell binding agent, and c) a membrane reagent layer; wherein the screen and each layer is in close and contiguous contact with the layer which follows it, and wherein at least one of layers a), b), and c) is conditioned by a pre-treatment.

The screen can have openings of from 10–200 microns. The blood cell binding agents are antibodies to red blood cells, chemical agents, or lectins. The separating layer has screen opening of preferably 20–200 microns.

8 Claims, 1 Drawing Sheet

DIAGNOSTIC TEST STRIP

BACKGROUND OF THE INVENTION

1. Field Of The Invention

This invention is directed to test strip devices and to analytical methods in which they are used. More specifically, this invention relates to test strip devices for determining the presence, absence and/or the amount of a substance in a liquid especially a biological liquid, and most especially blood. The invention includes strips for both clinical chemistry assays and immunoassays. This system accomplishes analysis of samples containing blood cells and other particulate matter with neither the prior separation of the solids from the sample, nor the requirement that excess sample be wiped away from the sample application site.

2. Description Of The Prior Art

The prior art contains an enormous amount of literature directed to analytical test strip devices ranging from simple layered devices of fibrous and non-fibrous materials to multilayered devices of mixed forms of layers such as fibrous and non-fibrous, synthetic or natural materials. Irrespective of the general form taken by the various test strips of the art, they tend to function by allowing the applied sample to migrate to a reaction site where the analyte of interest in the sample reacts with appropriate reactants. The evidence of the reaction is then viewed with the naked eye or through the detection of emitted energy under stimulation such as with a fluorometer, geiger counter, reflectometer, or the like. Some of the earlier systems described are those of U.S. Pat. Nos. 3,061,523 to Free, 3,552,925 to Fetter, 607,093 to Stone, 3,092,465 to Adams, and 3,630,957 to Rey.

In the Free patent a chemistry reagent system for colormetric determination of glucose in biological samples is described. A solid phase test strip is pre-treated with the reactants and thereafter contacted with a sample suspected of containing glucose. The intensity of color developed as a result of the reaction is compared to a control for an indication of the glucose level in the sample.

Fetter discloses a method and device for separating the whole blood sample into its liquid component and its red blood cell and other color forming component by pre-treatment of his test strip with water soluble salts. These salts separate the plasma from the red blood cells so that the plasma is free to wick into the test element.

In Fetter, the same element can be used for both the separating reagents and the reactants specific for the analyte of interest. The whole blood sample would be applied to one side of the strip held horizontally. After adequate penetration of the sample into the test strip, it would be inverted and any color change observed on the bottom of the strip.

U.S. Pat. No. 3,607,093 to Stone describes a liquid permeable membrane having within its matrix, a dry chemistry reagent system. Use of the Stone device requires the physical wiping of excess blood at the sample site of the membrane for removal of cells and other materials.

Lange U.S. Pat. No. 3,802,842 describes a test strip incorporating a dry chemistry reagent system in which a sample receptive surface of an indicator reagent layer is covered by a fine mesh. The indicator layer can be supported upon a colorless and transparent support. The addition of the fine mesh to this test element reportedly results in enhancement in speed and uniformity of distribution of sample upon the surface of the indicator layer. This uniformity of distribution also reportedly results in substantial improvement in reproducibility of result.

U.S. Pat. No. 4,042,335 describes a series of multilayered analytical elements suitable for performing chemical analysis of whole blood samples. They al contemplate the application of test samples either directly, or from a spreading layer, onto a reagent layer.

U.S. Pat. No. 4,144,306 (to Figueras), describes a multi-layered analytical element analogous to that of the Clement patent.

U.S. Pat. No. 4,258,001 to Pierce et al., describes a multi-layered analytical element (of the type described in both Clement and Figueras—previously discussed) incorporating a unique spreading layer. The spreading layer of the Pierce patent is described as an essentially "non-fibrous" material.

The above are only a small sample of various relevant pieces of prior art which relate to the analysis of blood and other liquids. Generally, a multilayer device is encountered, although single layered devices are used as well. More recently there have been single layered membranes used without any separating layers, but these generally allow red blood cells to come through to the reaction site.

SUMMARY OF THE INVENTION

The present invention is directed to a multi-layered test strip device for receiving whole blood on which a test for a suspected analyte is performed. The test will confirm the presence, absence, or the amount of analyte, if present. The multi-layered device comprises two outside support layers between which are, in descending order relative to the horizontal plane, a) a spreading screen having defined characteristics, b) a separating layer which removes red blood cells at least partially, and c) a membrane reagent layer; wherein the screen and each layer is in close and contiguous contact with the layer which follows it, and wherein at least one of layers a), b), and c) are conditioned by a pre-treatment.

DETAILED DESCRIPTION OF THE INVENTION

The operative layers of the test strip device of the present invention are uniquely structured and assembled. The invention contemplates both specific pre-treatment of at least one of the layers and a unique assembly thereof into a composite structure. In a preferred use of the test strip device, wherein whole blood from a finger stick for example, is used as the sample, a large number of the red blood cells from the sample are removed before the liquid part of the applied sample reaches the membrane. Thereafter, the membrane itself excludes the remaining red blood cells from the liquid advancing through the membrane such that virtually red cell-free plasma reaches the viewing site of the membrane as discussed below.

Figure 2:
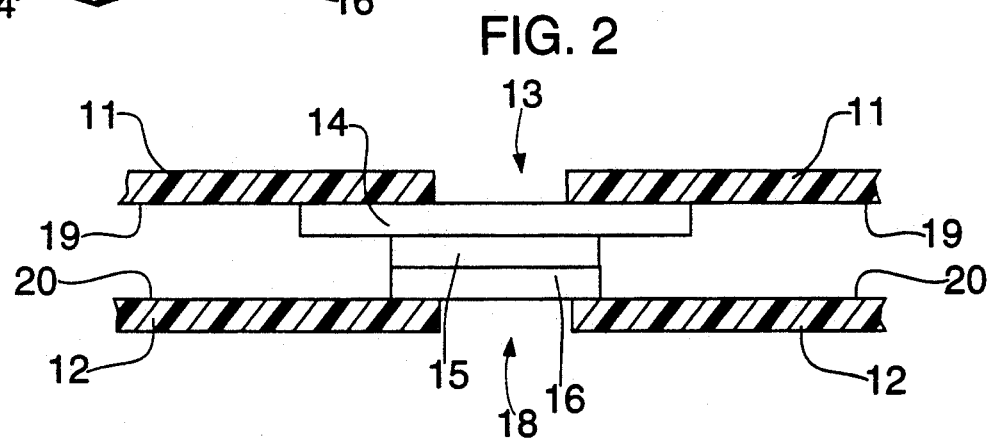
FIG. 2 is a cross section elevation view of the test strip of FIG. 1 at A—A.

In this regard, and turning now to the Figures, the three operative layers 14, 15, and 16 are bound tightly to the inert support strips 11 and 12. The support strips are preferably constructed from mylar. A layer of glue is provided on the interior surfaces of the supports 11 and 12 shown at 19 and 20 of FIG. 2. The glue physically attaches the supporting layers to each other resulting in a compression of layers 14, 15, and 16.

Next, in descending order, the separating layer 15 abuts the spreading screen 14 at its uppermost surface and meets the reaction membrane layer 16 at its lowermost surface. The reaction membrane 16 is glued onto the inert support 12. The stack comprising the layers 14, 15, and 16 are aligned vertically with blood sample receiving port 13 and reaction viewing port 18. Ports 13 and 18 are openings in the mylar support strips 11 and 12 and the elements 13, 14, 15, 16, and 18 constitute the vertical alignment along which the sample flows. Spreading screen 14 greatly overextends the separating layer 15 in order for it (the screen) to become attached to the glued surfaces and therefore further ensure a tight, secure contact of layers 14, 15, and 16 between and among each other. It is to be noted that there is no glue between layers 14 and 15, and between layers 15 and 16.

In use, blood or other sample is applied to the device at sample port 13 where it meets spreading screen 14. When blood is being analyzed, the drop applied is often obtained from a finger stick and is of the order of 10-50 microliters. The sample reaches the spreading screen 14 and is held there momentarily by the surface tension created by the openings of the screen, of which more will be discussed later. When sufficient sample has contacted the spreading screen to overcome surface tension, a sudden burst of sample passes directly from screen 14 to the separating layer 15, uniformly across the surface of the spreading layer, thus avoiding the consequences of unevenly applied sample discussed below.

At separating layer 15, red blood cells are at least partially removed owing in part to the presence on the separating layer of an agent or agents whose task is to bind red blood cells. The resulting plasma portion of the applied blood sample includes at this point enough residual red blood cells to cause a problem in later reading if they are not removed, then moves onto the reaction membrane 16 and then through the membrane therein to contact the reagents residing in membrane 16 which are specific for reaction with the analyte of interest. The membrane also includes an indicator system indicative of a reaction product between the analyte and the specific reagents. It is highly desirable that when blood is used as the sample, virtually no red blood cells reach the reading port 18 of the reaction membrane 16 where the color of the red blood cells would interfere with the visualization of the reaction product between the analyte, its specific reactants, and the indicator system. This invention achieves this result.

An important feature of the invention is the fact that the various layers are brought into tight and secure contact with each other and maintained in that position via bonds 17A, 17B, 17C, and 17D. These bonds are the result of applying energy, such as ultrasonic energy, to the strip from a point source applied to the upper surface of strip 11 during assembly and while shown as dotted lines in FIGS. 3 and 4, in practice will be more likely pinched indentations in the assembled strip. This results in the localized welding of the support strips to each other through the screen 14 in the cases of points 17A and 17B, and through the screen 14, the separating layer 15, and reaction membrane 16, in the case of points 17C and 17D. Other locations can be chosen as long as there results an intimate, tight contacting of the relevant surfaces so as to minimize pooling of small portions of plasma between the surfaces. To the extent there is such pooling, the advantages of this invention relating to a lower blood sample requirement is proportionately reduced.

Figure 4:
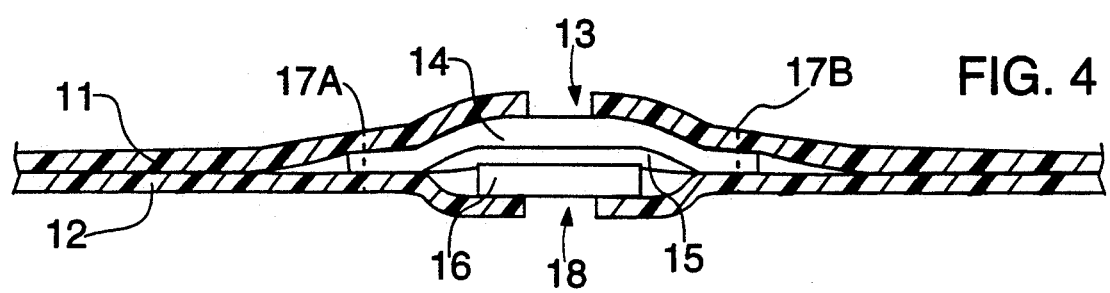
FIG. 4 is a cross sectional elevation view of another embodiment of the invention along a similar cross section line to that of FIG. 1 as it appears after construction (not to scale).

As inert support strips there may be used any materials which give rigid support to the test strip and do not interfere with the fluid sample or the test reactants. For example, there may be used pressed, non-absorbing paper or cardboard, plastics of various kinds such as mylar, polyethylene, polypropylene, or the like. Mylar is preferred. Glue is provided on the interior surfaces of mylar strips 11 and 12 at surfaces 19 and 20 to form the anchoring means for the spreading screen 14 and the reagent membrane 16 and when appropriate, separating layer 15 as shown in FIG. 4.

The characteristics of the spreading screen 14 are important. While the material of construction of the screen may be any which does not alter the test results, we have found that best results are obtained with a structure of nylon, silk, polyester, polyethylene, or polypropylene. Most preferred is polyester. It is important that the mesh openings have a direct uninterrupted pathway from the upper surface where sample is applied to the separating layer 15 as they would in a window screen, sieve, or netting material. Thus, as used herein, the term "screen" is meant to apply to mesh openings that would allow a beam of light to pass directly through the screen as opposed to carded or nonwoven structures which would allow fluids, but not direct light, to pass through.

The purpose of screen 14, in the test strip device is to spread the sample applied at 13 laterally over the screen and retain it there momentarily before any of the sample is permitted to pass through to the separating layer 15. This ensures that the sample will pass through the screen uniformly onto the surface of the separating layer 15. This is important because a non-uniform distribution of the sample to the separating layer will inevitably cause a non-uniform distribution of separated plasma to the reaction membrane which in turn will result in a mottled coloration of reaction product and/or a loss of precesion in results owing to the differences in reaction time of the analyte in the sample with reactants.

An appropriate screen is therefore one which has mesh openings sufficiently small to provide an adequate retention time of the applied sample to allow complete lateral contact of the screen, but yet not so small as to require inordinate amounts of liquid sample to break through the surface tension. Nor should the screen be so thick as to require larger amounts of sample. For blood samples, screens having mesh openings of 10 to 200 microns and preferably 15 to 150 microns depending upon the material of construction, are suitable. Screens having a thickness of 25 to 150 microns and preferably 50 to 125 microns are suitable for use in the invention. Such screens are readily commercially available in a variety of materials of construction. We prefer a polyester screen having a thread diameter of between 20 to 50 microns and a screen thickness of from 50 to 100 microns.

The separating layer 15 is, typically in the invention, a fabric screen material which when treated according to the invention separates a large portion of the red blood cell component from the blood sample passing from screen 14. Thus, the material which initially reaches the uppermost surface of membrane 16 is plasma containing some proportion of red blood cells usually not more than about 20%. Whatever red blood cells are present at that point are separated from the plasma at or just below the surface of the reaction membrane because the membrane, as noted below, is selected for properties which would provide such separation. Thus the remaining portion of originally applied sample which reaches the lowermost, reading surface of the membrane 16 is plasma with essentially no red blood cells detectable within the timeframe of the test.

To aid in the removal of the red blood cells from blood so that a clear liquid plasma sample for testing can be obtained, the separating layer 15 is treated before assembly with one or more agents having the capacity to bind or adhere to red blood cells without lysing them so as to avoid releasing red coloration to the reaction membrane. The binding agents capture the red blood cells and hold them on the separating layer.

The binding agents will be described in more detail below. It is a critical point of this invention, however, that the material of construction of the separating layer be such as to minimize the absorption capabilities of the separating layer per se. The object is to avoid or minimize the absorption of plasma at the separation layer and maximize the plasma which reaches the reaction membrane. This results in requiring less blood from the patient. The art is fully cognizant of the difficulties many patients experience in obtaining a sufficient amount of blood sample from a finger stick suitable for analysis. The prior art usage of porous, absorbent filters as separating layers is very wasteful of the applied blood sample, resulting in an inordinate amount of plasma being absorbed by the filter instead of being available for analysis.

A further advantage of the device of the present invention is in the uniformity of the readable reaction results on the underside of the reaction membrane at 18. The present invention is insensitive to the mode of application of the blood because the parameters of the initial spreading screen lead to the lateral flow of blood sample when applied to the screen and the subsequent uniform depositing of the blood on the separating layer. This combined with the general openness of the treated separating layer 15 ensures a uniform depositing of the plasma with some red blood cells onto the reaction membrane. The more uniform the depositing onto the membrane, the greater the likelihood of obtaining uniform color development at the reading site 18 of the membrane.

The criteria we have found to be useful in selecting a fabric for a separation layer are as follows:

a) mesh size openings are smaller than the mesh size opening of the spreading screen, preferably from 20 to 200 microns.

b) open area (that is percent of fabric occupied by voids) 15–60 percent.

c) openings are "screen" openings.

Preferred for use in the invention is a single layer of a fabric of polyester, cotton, or a 50% polyester/50% cotton blend.

The blood cell separating agents which may be used are any of a variety of agents normally known in the art to bind to red cells without lysing them. Such agents have been described in the literature. For example, antibodies to red blood cells, water soluble salts having an inorganic cation such as potassium citrate, ammonium sulfate, zinc sulfate, and the like, see e.g. U.S. Pat. Nos. 3,552,925 and 3,552,928 to Fetter and lectins may be used. Lectins are particularly suitable. Lectins are proteins or glycoproteins that recognize specific sequences of polysaccharide residues. They are found in plants, seeds, and organisms.

Numerous lectins are commercially available. Some commercially available lectins and the specific sugar residues they recognize are Concanavalin A (Alpha-glucose and alpha-D-mannose), soybean lectin (D-galactose and N-acetyl-D-galactosamine), wheatgerm lectin (N-acetyl glucosamine), lotus seed lectin (fucose), potato lectin (N-acetyl glucosamine), dilichos biflorus agglutinin (N-acetyl galactose-aminyl), and legume derived lectins such as lentil lectin (Alpha-D-mannose and alpha-D-glucose).

We prefer to use a lectin as the red cell binding agent and in that regard, prefer a legume-derived lectin. The lectin or other binding agent is applied by dipping the separating layer fabric into a solution of the lectin or other agent and allowing the wetted fabric to air dry. The solution can be prepared in concentrations that are easily handled in standard test strip manufacturing equipment. Typically, 2–7% solutions are acceptable.

The porous reaction membrane which contains the relevant reagents within its matrix may be any of the type normally used in the art such as those referred to in the Stone U.S. Pat. 3,607,093, in Terminiello U.S. Pat. Nos. 4,774,192 and 4,790,979, and in Kondo U.S. Pat. No. 4,256,693, the disclosures of which are incorporated herein by reference.

Best results are obtained from the reaction membrane when it contains, in addition to the specific reagents needed for the analysis, certain conditioning agents which improve the performance of the reaction membrane. The conditioning agents are generally incorporated into a blend of the reactants before the latter are incorporated into the reaction membrane. For example, when preparing a reaction layer for a glucose test strip, a base solution of an enzyme necessary for the reaction, e.g. catalase in a liter of solution is prepared with citric acid, PVP and BSA and serves as the base to which the chromogen indicator system and other reactants, i.e. peroxidase and glucose oxidase are added. We have also found that the color generation by the reaction is stabilized and its readability enhanced by adding a small amount (0.0005–0.009 ml/L of solution) of DOSS (dioctyl sulfosuccinate sodium) available from Sigma Chemical Company.

Further, the addition of Gantrez AN 139 (a 2,5 furandione polymer with methoxyethene otherwise known as a methyl vinyl ether copolymer with maleic anhydride) at a level of about 0.0005–0.009 ml/L of solution aids as a conditioner of the membrane.

The prepared solution may be applied to the membrane as by dipping and the saturated membrane allowed to air dry.

As the reaction membrane per se, different materials may be selected for differing analytes, but in the determination of glucose, we prefer to use a hydrophilic polysulfone membrane having a pore size of 0.2–0.8 microns. We prefer to use the Supor[R] series of membranes from Gelman Sciences of Ann Arbor, Michigan, 48106.

An important feature of the present invention is that in the construction thereof, effort is made to cause a tight fitting of the layers to one another. It has been found that the standard techniques of gluing the operative layers to the interior surfaces of the support strips is not sufficient to produce a tight unitary structure. We have found that the extraordinary method of ultrasonically bonding the layers produces best results. In pursuing this approach, care should be taken to avoid spillover of the energy source onto the sample application zone and the reading site on the underside of the reaction membrane.

The following example illustrates a preferred embodiment of the invention.

EXAMPLE

1. A polyester medical screen designated PeCap/-7-16/8 available from Tetko,Inc., Elmsford, New York and having a mesh opening of about 16 microns, a thickness of about 75 microns and an open area of voids of 8% is dipped into a 10% solution of sodium chloride and allowed to dry.

2. A woven fabric of 50% polyester/50% cotton having "screen" openings of about 25 microns, open voids area of 16–20% and a thickness of about 0.010 inches is dipped into a 2% solution of a lectin derived from kidney beans and allowed to air dry.

3. A solution of 4 gms Citric Acid (free acid monohydrate), 54g of Citric Acid (otrisodium salt dihydrate), 60g polyvinylpyrrolidone, 50 IU/L catalase and 4g bovin serum albumin (BSA) is prepared. To 0.933 ml of this solution is added 0.0055 gm O-Tolidine-Hydrochloride, 0.067 ml deionized water, 0.0075 gm BSA, 0.0003 gm glycerol, 11.0 IU peroxidase, 9.5 IV glucose oxidase, 0.002 ml DOSS, and 0.003 ml of Gantrez AN-139.

A six inch wide membrane of Supor 450, pore size 0.45 microns is dipped into the above solution at a rate of 7 ml of solution applied per linear foot of membrane and allowed to air dry.

Figure 1:
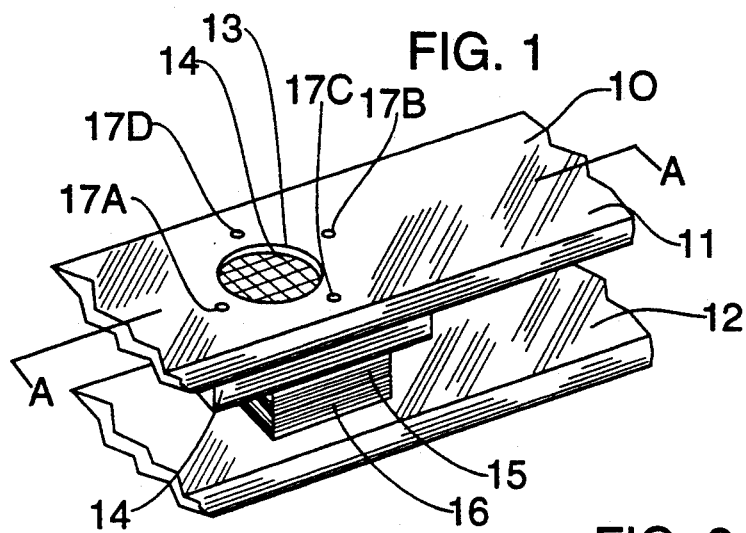
FIG. 1 is a perspective view of the test strip device (not shown to scale) of the invention.
Figure 3:
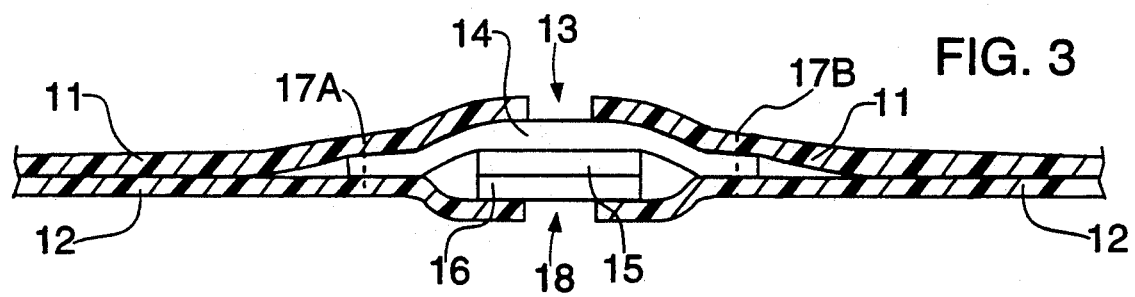
FIG. 3 is a cross section elevation view of the layers of the test strip at A—A of FIG. 1 as it appears after construction (not to scale).

The above layers are assembled in the configuration shown in FIG. 3 using standard techniques in the art and using mylar strips (having the appropriately placed ports and openings) as the support medium for the interior three layers. The inside surfaces of the mylar strips have been previously treated with glue to hold the screen and the reaction membrane in place. In some applications it is desirable to select a separating layer 15 which is slightly larger in width than the reaction membrane so that the edges of the separating layer 15 may overlap the reaction membrane 16 and meet the mylar strip 12 at the glued surface to aid further in securing the separating layer to the rest of the device. (See FIG. 4.) Once these layers have been assembled, the test strip is inserted into an ultrasonic point welding device and the strop welded at the points shown at 17A, 17B, 17C, and 17D in FIG. 1. A suitable strip is 2 inches long by 0.5 inches wide by 0.035 inches thick with a sample port 13 and viewing port 18 of about 0.2 inches in diameter.

In use, one places a drop of blood of about 25 uliters, from a finger stick for example, onto the screen surface. The invention can work well with from 10 to 50 ul of sample.

We have found that suitable results are obtained in a glucose test when the plasma separated from the applied blood is allowed to react for a pre-determined period of from 35–50 seconds, preferably 40–45 seconds at the reaction membrane. The color obtained at the reading site of the reaction membrane after the set period of time has elapsed is compared to a control or standard and thus us correlated to the amount of glucose in the original sample. The reading can be done by the naked eye and compared to color charts of varied and defined color intensities at various concentrations of glucose. We prefer to use a reflectance reading on the reacted color which is compared in a computer analysis to standard reflectances obtained on known concentrations of glucose in reaction with the membrane reactants.

The above procedure has been used to prepare hundreds of test strips which have been used in analysis on controls and standards as well as on actual patient blood containing unknown amounts of glucose. The results obtained from using the strips in the above manner have a correlation coefficient of about 0.95 when compared to the results obtained on a Yellow Springs Instrument Company, Yellow Springs, Ohio 45387, Stat Whole Blood Glucose Analyzer, Model No. 2300.

What is claimed is:

1. A test strip device for measuring an analyte in a liquid sample consisting essentially of relative to a horizontal plane,
    a) a top support layer which provides support to the test strip device, such layer having a sample receiving port therein,
    b) a spreading screen physically attached to said top layer and located directly below said sample receiving port whereby sample applied at said port encounters said screen, wherein said screen has mesh openings sufficient in size
        i) to act as a retaining screen for said sample until substantially all of such screen in said port has been contacted with said sample, and
        ii) to allow the sample to proceed vertically through the screen in a uniform flow,
    c) a screen mesh separating layer adjacent to and in contact spreading screen in vertical alignment with said sample port, said layer having fixed thereon an agent capable of capturing red blood cells,
    d) a reaction membrane having a surface which is in direct physical contact with said separation layer, said reaction membrane
        i) being capable of excluding red blood cells from a liquid sample containing the same, and
        ii) having reactants and an indicator system incorporated within its matrix capable of reacting with the analyte of interest in the sample and causing a color change at the reaction membrane which is a measure of the presence or amount of analyte in the sample, and
    e) a bottom support layer in physical contact with said reaction membrane and which provides support to the test strip device, said layer having a reaction viewing opening in vertical alignment with the sample receiving port.

2. The test strip of claim 1 wherein the screen mesh openings are from 50–200 microns.

3. The test strip of claim 2 wherein the mesh openings of the separating layer are smaller than the mesh openings of the spreading screen.

4. The test strip of claim 1 wherein the mesh openings of the separating layer are between 10–200 microns.

5. The test strip of claim 4 wherein the mesh openings of the separating layer are between 50-100 microns.

6. The test strip of claim 5 wherein the red blood cell binding agents on the separating layer are lectins.

7. The test strip device of claim 1 wherein the spreading screen is a single layer, the separating layer is a single layer, and the reaction membrane is a single layer.

8. The test strip device of claim 1 wherein the reactants and the indicator system incorporated into the membrane are specific for the determination of glucose in blood plasma.

* * * * *

UNITED STATES PATENT AND TRADEMARK OFFICE
CERTIFICATE OF CORRECTION

PATENT NO. : 5,296,192
DATED : March 22, 1994
INVENTOR(S) : Patrick J. Carroll and Robin Wiscovitch It is certified that error appears in the above-indentified patent and that said Letters Patent is hereby corrected as shown below:

<u>Column 8, line 43</u> after the word "contact", insert ...with the...

Signed and Sealed this

Fifth Day of July, 1994

Attest:

BRUCE LEHMAN

*Attesting Officer*     *Commissioner of Patents and Trademarks*